(12) United States Patent
Chiang

(10) Patent No.: US 6,341,878 B1
(45) Date of Patent: Jan. 29, 2002

(54) METHOD AND APPARATUS FOR PROVIDING UNIFORM DIFFUSE ILLUMINATION TO A SURFACE

(75) Inventor: Gilbert W. J. Chiang, San Francisco, CA (US)

(73) Assignee: Cognex Corporation, Natick, MA (US)

( * ) Notice: Subject to any disclaimer, the term of this patent is extended or adjusted under 35 U.S.C. 154(b) by 0 days.

(21) Appl. No.: 09/387,159

(22) Filed: Aug. 31, 1999

(51) Int. Cl.$^7$ ................................................ F21V 9/00
(52) U.S. Cl. ........................ 362/293; 362/30; 362/19; 362/583
(58) Field of Search ...................... 362/19, 30, 293, 362/355, 551, 554, 558, 575, 583; 356/394, 236; 359/386, 389

(56) References Cited

U.S. PATENT DOCUMENTS

| | | | |
|---|---|---|---|
| 3,292,490 A | * 12/1966 | Moore | 356/394 |
| 3,711,701 A | * 1/1973 | Squyres | 356/394 |
| 5,024,525 A | 6/1991 | Yoshida | 354/126 |
| 5,172,005 A | 12/1992 | Cochran et al. | 250/57 |
| 5,416,594 A | 5/1995 | Gross et al. | 356/237 |
| 5,684,530 A | 11/1997 | White | 348/131 |
| 5,842,060 A | 11/1998 | White et al. | 396/155 |
| 5,847,822 A | 12/1998 | Sugiura et al. | 356/239 |
| 5,997,164 A | * 12/1999 | Betts et al. | 362/575 |

FOREIGN PATENT DOCUMENTS

| | | |
|---|---|---|
| EP | 0446838 A2 | 9/1991 |
| EP | 0935134 A1 | 8/1999 |
| JP | 05088239 | 4/1993 |

OTHER PUBLICATIONS

Advanced Illumination; DL9160 Diffuselite; 04/07/99; pp. 1–2.
PCT International Search Report, Jan. 29, 2001.

* cited by examiner

Primary Examiner—Y. My Quach-Lee
(74) Attorney, Agent, or Firm—Williams A. Loginov; Russ Weinzimmer

(57) ABSTRACT

A method and apparatus for providing a uniform illumination to a part provides a backlight unit in the form of a light panel located beneath the part. A reflector, generally hemispherical in shape, is located over the part to receive reflected light from the backlight. A first plane-polarizing material is positioned over the backlight, also beneath the part, and a second plane polarizer is located adjacent an aperture at the apex of the hemispherical reflector. A camera, mounted external of the reflector, is positioned to receive light passing through the second polarizer. Transmitted light from the backlight is polarized by the first polarizing material as it is transmitted to the reflector. Light directly received by the camera is filtered-out by the second polarizer, while reflected light that illuminates the part can substantially pass through the second polarizer into the camera.

19 Claims, 3 Drawing Sheets

METHOD AND APPARATUS FOR PROVIDING UNIFORM DIFFUSE ILLUMINATION TO A SURFACE

FIELD OF INVENTION

This invention relates to illuminators and more particularly to illuminators for use in machine vision systems for inspection of irregularly shaped surfaces.

BACKGROUND OF THE INVENTION

It is often desired to inspect objects during manufacture for imperfections, and to verify proper size, shape and surface characteristics. Such inspections can be part of an overall quality control process undertaken during manufacture. The inspection procedure can be performed using automated equipment, or by an operator who visually inspects each part as it passes through an inspection station. Parts are typically transported to and from the inspection station by a moving conveyor belt, robot arm or other transport mechanism. Surface imperfections, and other irregularly shaped formations on a part, may extend transversely to the flat surface under view-thereby requiring specialized illumination to be properly viewed. In general, such specialized illumination is generated by a diffuse lighting source.

FIG. 1 shows a generalized illumination system for inspecting irregularly shaped parts according to the prior art. The system 10 includes a base 12 upon which a part to be inspected 14 is located. The upper supporting surface 15 of the base 12 can have a variety of shapes, colors and reflectivity depending upon the inherent optical characteristics of the part 14. In many systems, the surface 15 is matte black in reflectivity and color. The base 12 can be a moving surface such as a conveyer belt or other transport mechanism for carrying parts through the inspection system 10, as noted above.

The part 14 is located on the surface 15 directly beneath a combination light source/reflector assembly 16. The clearance C between the bottom rim of the reflector assembly and the surface 15 is usually sufficient to enable the part to pass thereunder without requiring axial (up and down) movement of the reflector assembly 16 or base 12. The inner surface 18 of the reflector assembly 16 defines the interior of a hemisphere in a typical system arrangement. The surface 18 is coated with a matte white coating to generate a highly diffuse reflected light from any light striking the surface. The illumination light is, itself, provided by a ring illuminator 25 constructed integrally within the reflector assembly. Specifically, the bottom edge 20 of the reflector assembly 16 includes a well 22 with an inner upstanding wall 24. This well, defining an annular channel, houses the light elements of ring illuminator 25. The ring illuminator 25 is generally formed from a series of LEDs 26 arranged at even intervals around the perimeter of the edge 20. Fiber optic tips or other light sources can also be employed. The ring illuminator 25 generates a series of rays (shown schematically as arrows) 30 that strike the part 14 in an indirect manner. As such, the exposed surface of the part is illuminated effectively with a largely diffuse, indirect light.

During inspection, the illuminated part 14 is viewed through an aperture 32, located at the apex of the hemisphere. In the typical system a camera assembly 34 is mounted at an appropriate focal length above the aperture for remote viewing of the part. The camera assembly 34 can comprise any acceptable, commercially available solid-state camera unit usually adapted to transmit real-time image data of viewed subjects. The camera assembly 34 can include a telecentric lens arrangement 35 according to a conventional design. This type of lens selects light rays that are oriented generally parallel to the axis (dashed line 37) of the camera 34. The lens can include a zoom function and inherent magnification as well as internal aperture (F-stop) control.

A typical camera assembly for use in the illustrated system employs a solid state CCD element that generates an image signal for transmission via a data line 36. This image signal is carried over the line 36 to an image processor/frame grabber 38. The image processor/frame grabber 38 typically acquires a single image or set of frames showing the viewed part, and may be programmed to provide digital enhancements to various portions of the image. The captured image is displayed on a video display 40. Various input/output (I/O) peripherals can be provided to control the image processor/frame grabber 38. These can include various microprocessor functions accessed through a keyboard, mouse or graphical user interface. As noted above, the process can be automated.

The above-described inspection system 10 has the disadvantage that the ring illuminator 25 is located at a significant distance (clearance C) above the part 14. In addition, the upstanding wall 24 of the illuminator housing further blocks illumination light at lower angles of incidence with respect to the part 14 and underlying surface 15. The higher-angle rays 30 shown are less capable of fully illuminating side edges (for example edge 44). As such, structures and edges on the part that require low-angle illumination for proper definition are less well-defined.

A further disadvantage of the illuminator according to FIG. 1 is that the size and shape of the reflector assembly 16 limits the variety of illumination structures that can be employed as well as the color and intensity of the illuminator. In addition, the reflector must include various electrical connectors and leads when incorporating an illuminator therein. These overhead connections and leads can be cumbersome, and can sometimes impede movement of parts and equipment about the manufacturing floor.

Accordingly, it is an object of this invention to provide a method and apparatus for illuminating parts with a uniform diffuse light that enables lower-angle light rays to strike the part. This invention should decrease the complexity of the reflector by removing various elements for integral illuminators and should enable a wider range of illumination colors, intensities and light characteristics to be employed.

SUMMARY OF THE INVENTION

This invention overcomes the disadvantages of the prior art by providing an illuminator in the form of a backlight unit upon which the part is directly supported while a hemispherical-shaped reflector is positioned above the part, free of a ring illuminator thereon, so that light is reflected onto the part at a lower angle with respect to the supporting base. This more-fully illuminates side edges and upright surfaces on the part for enhanced viewing of these features. An aperture is located at the apex of the reflector, overlying the part. A camera or other viewing device is positioned over the aperture. Through the use of a plane polarizer on the backlight and on the camera lens, any light transmitted directly from the backlight to the camera is filtered-out, while indirect light bounced from the reflector back onto the part is substantially fully viewed.

In a preferred embodiment, the edges of the reflector are brought as close as possible to the level of the part without obstruction by the upstanding walls of an integral illuminator. As such, lower-angle incident light is effectively transmitted onto the part for viewing by a camera. This camera is mounted above an aperture at the apex of the reflector. The reflector can define a hemisphere with a matte white inner surface for providing a highly diffuse light. Alternatively, a different geometry can be employed and/or a different reflector surface characteristic is contemplated. The backlight unit, according to a preferred embodiment, comprises a commercially available structure having an upper diffuser plate and a grid of upturned fiber optic tips mounted thereebeneath to generate a wide field of diffuse, uniform light. In particular, the tips are formed on the ends of a series of respective fibers that are collected into a cable bundle. The cable is itself connected to a high-intensity light source. Various filters, controllers and selected bulb intensities can be used to vary the characteristic of light provided to the backlight unit by the light source. A variety of part transport mechanisms including conveyer belts, trolleys and robot arms can be incorporated into the system of this invention. The reflector is located so that it provides clearance for parts to pass into and out of the inspection area thereunder.

BRIEF DESCRIPTION OF THE DRAWINGS

The foregoing and other objects and advantages will become more clear with reference to the following detailed description as illustrated by the drawings in which.

DETAILED DESCRIPTION OF AN ILLUSTRATIVE EMBODIMENT

Figure 1:
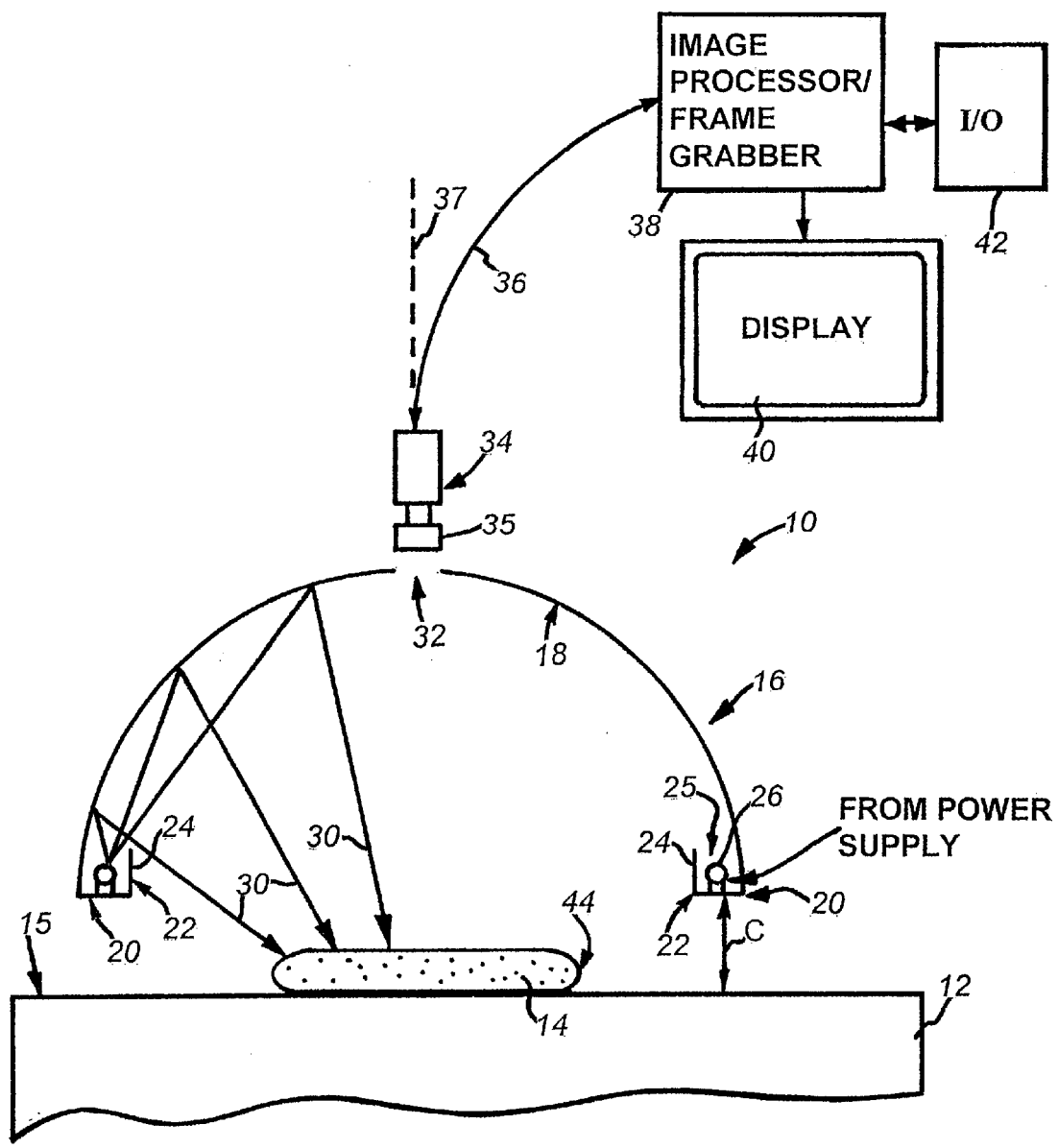
FIG. 1, already described, is a schematic cut-away view of a part inspection system including a combined illuminator and reflector assembly according to the prior art.
Figure 2:
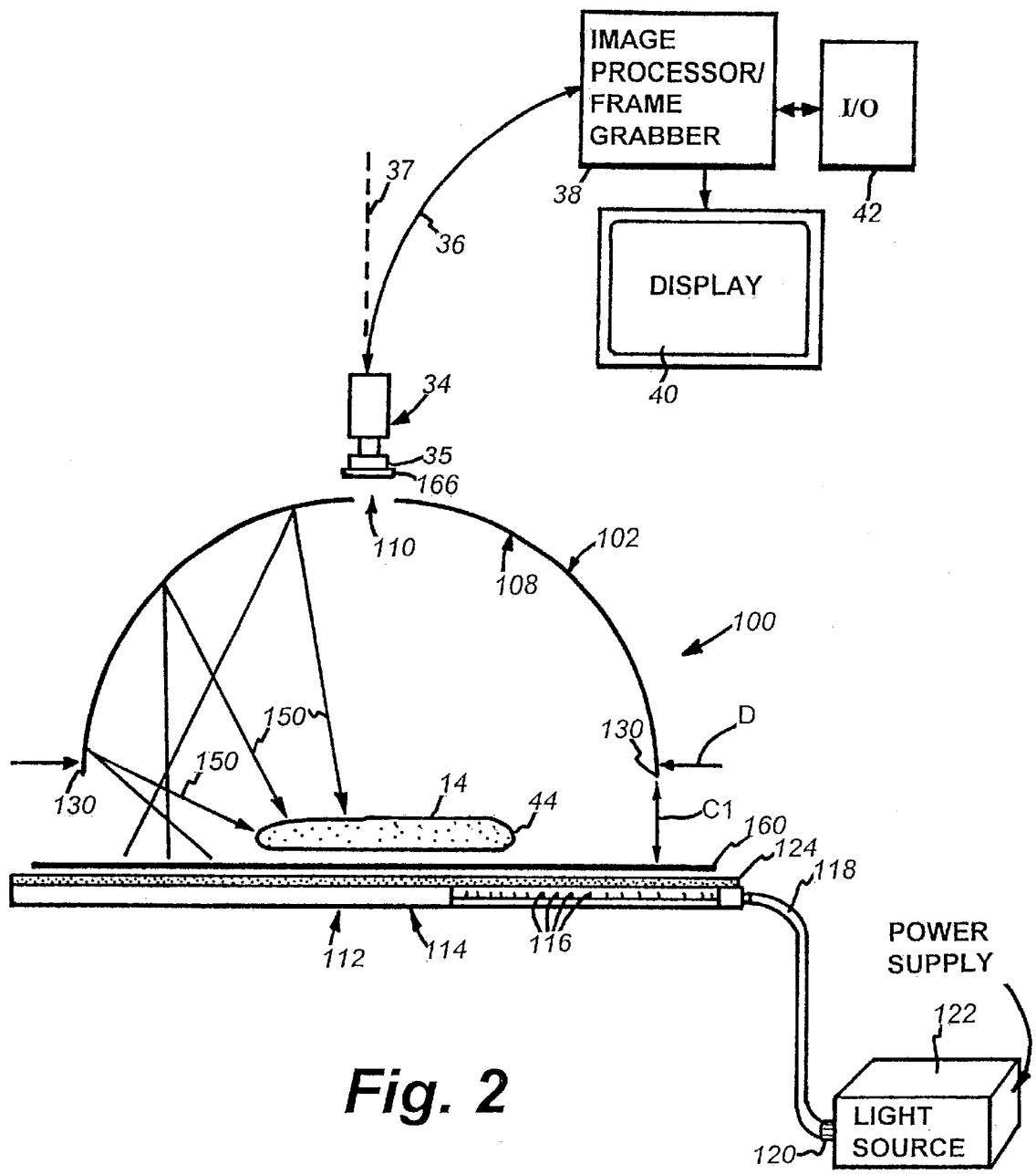
FIG. 2 is a schematic cut-away view of an inspection system including a backlight illuminator base and associated overhead reflector assembly according to this invention.
Figure 3:
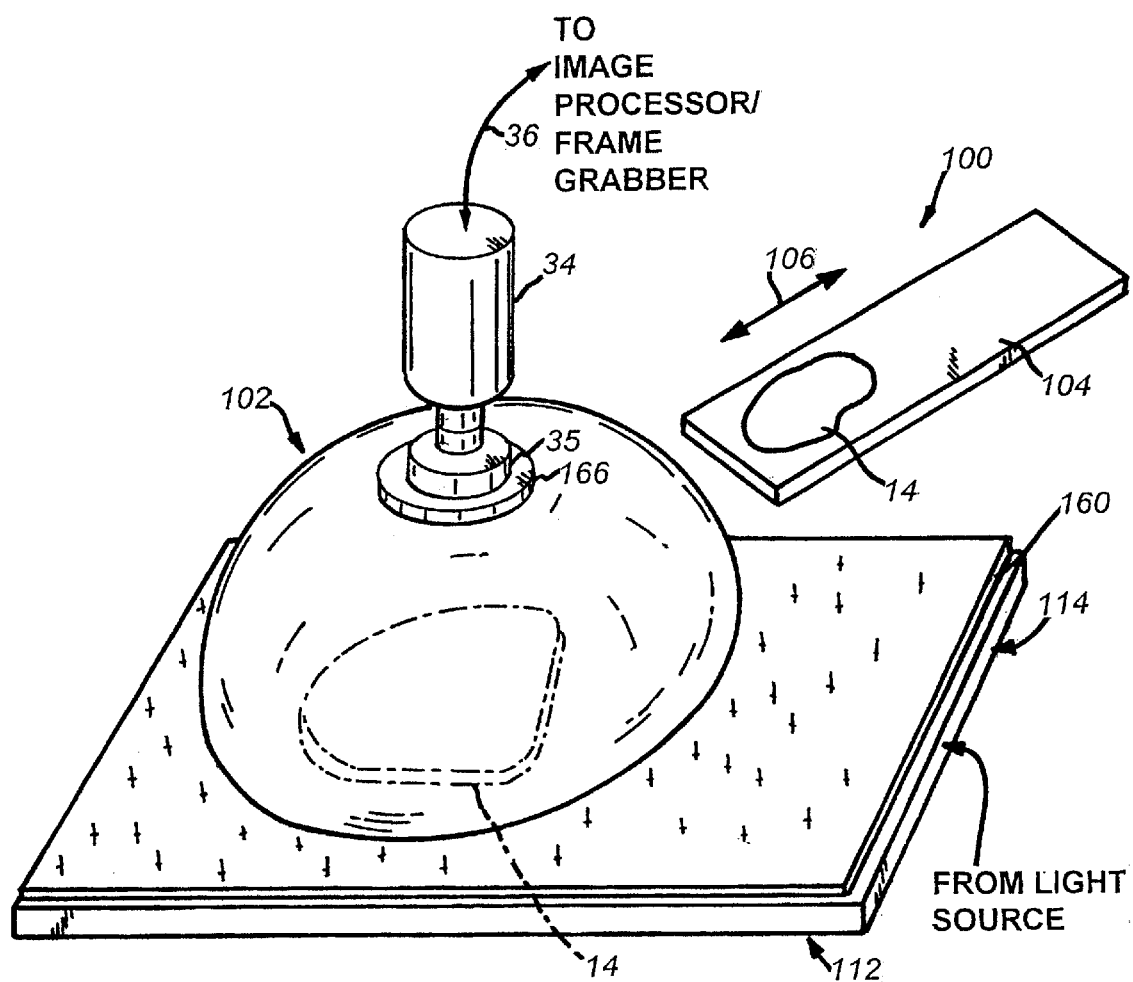
FIG. 3 is a schematic perspective view of the system of FIG. 2.

A system for illuminating a part for inspection, according to this invention, is detailed in FIGS. 2 and 3. The system 100 includes a camera assembly similar to that described with reference to FIG. 1 above. Where the same or largely similar components are detailed, like reference numbers are used. In general, the camera assembly 34 includes a telecentric lens 35. It is interconnected with an image processor/frame grabber 38 that routes image signals to a display 40 over a line 36. Various I/O devices 42 can be used to program and control the image processor/frame grabber and display. The camera assembly 34 is aligned along a vertical axis 37 that is the optical axis for the according to this description. This axis 37 is generally perpendicular to the base on which the part is supported, but it can be translated into a variety of non-perpendicular orientations if necessary for accomplishing a particular part-inspection task. The camera assembly 34 is supported by brackets (not shown) that can be attached to an overhead stand or directly to the underlying reflector assembly 102. Likewise, the reflector assembly 102 can be supported by brackets (not shown) that maintain it in a suspendended orientation so that a part 14 to be inspected can pass thereunder. With reference particularly to FIG. 3, a part 14 is transported into and out of the inspection area on a transport arm 104 (see double arrow 106). A variety of transport mechanisms including conveyer belts, moveable arms, wheeled trolley mechanisms, and the like, can be employed to move parts into and out or the inspection system 100 according to this invention. These transport mechanisms in general should enable the part to be located at a predetermined position within the inspection system to increase the predictability of the inspection process. The arms can also be adapted to enable the part to be moved about within the inspection area so that various aspects of the part can be viewed from different perspectives. The arm can be adapted to release the part so that it stands alone within the inspection area, or it can be adapted to remain in contact with the part during inspection. It is desirable that where the arm remains, its profile be limited so that it does not extend substantially beyond the outline of the part, thus obscuring the illuminator light (as will be described further below).

The reflector assembly 102 comprises a hemispherical shell according to this embodiment. It is expressly contemplated that a variety of reflector shapes can be employed herein including a half-cylinder, angled planes, ellipsoids, and any other specialized shape that may be particularly suitable to view a specific type of part geometry. Accordingly, the term "reflector" as used herein should be taken broadly to include any shape or form of reflector surface that bounces a diffuse light from a source onto an underlying part.

The illustrated reflector 102 includes an inner surface 108 having, in this embodiment, a matte white coating. According to an alternate embodiment, the color of the coating, can be varied to suit the particular optical characteristics of the underlying part and illuminator light. For example, a non-specular silver reflector surface can be substituted. In addition, the reflector can be specular in whole or in part according to another alternate embodiment.

At the apex of the reflector assembly 102 is located a circular aperture 110. The aperture 110 is sized to enable the camera assembly 34 to view the part 14 fully, according to this embodiment. It is generally desirable to optimize the size of the aperture so that it is not excessively large. However, the exact size and shape (circular, square, ovular, etc.) is widely variable. In addition, the field of view and magnification of the camera can be widely varied. In this embodiment, the reflector has an overall diameter D that is approximately twice the size of the largest part to be passed there under.

According, to this embodiment that part 14 is supported on a base 112 that includes a backlight unit 114 according to a preferred embodiment. It is contemplated that the part may be supported directly on this backlight unit, or suspended at a predetermined distance thereabove. Generally, the backlight unit 114 it is provided beneath the part and, as such, the part lies between the backlight unit 114 and the reflector assembly 102. The backlight unit 114 delivers a roughly uniform diffuse light over its entire surface. One popular form of backlight unit includes a grid of individual optical fibers (cutaway in FIG. 2) having exposed tips 116 turned upward toward the upper face of the unit. Each of the fibers is part of a large bundle that is formed into a covered fiber optic waveguide cable 118. This cable is connected via a connector 120 to a conventional fiber optic light source 122. In a preferred embodiment, a commercially available backlight unit is available from Fostec, Inc. of Auburn, N.Y. as part no. A08927. This particular source is a square-shaped panel sized approximately eight inches by eight inches. The exemplary backlight unit mounts the underlying grid of upturned fiber optic tips 116 beneath an overlying diffuser panel 124. When driven by an appropriate light source 122, the fiber optic tip grid emanates a large number of point sources of light that are spread by the diffuser panel 124 into a fairly uniform diffuse light over the surface of the backlight unit. The panel 124 can include a variety of translucent surface finishes to generate a diffuse profile including frosting, diamond patterns and the like. The panel can be white/clear or have an embedded color. The light source 122 for driving the grid is also available from Fostec, Inc. as part no. A20520. In a preferred embodiment it includes 150-watt quartz halogen lamp, its self-driven by a 21-volt DC power supply.

As used therein the term "backlight" shall refer to any plate structure, either flat or having a non-flat surface geometry that transmits a relatively uniform diffuse light over all or a portion of its surface-in the manner generally of a "light panel." While a grid of fiber optic tips are used to generate the light according to this embodiment, is expressly contemplated that a grid of LEDs can be utilized or a series of bulbs, either incandescent or fluorescent. Similarly, groups of mirrors can also be used to generate a diffuse light panel effect. The size of the light panel used according to this invention can be widely varied. In general, the light panel is sized to extend beyond the perimeter edges of the reflector so that the area therebeneath is fully illuminated. The reflector is located so that its lower edge 130 (e.g. the reflector perimeter edge) is spaced at a spacing C1 away from the base 112. As noted above, this enables a part to be moved into and out of the reflector area with ease. The spacing C1 of the lower perimeter edge 130 of the reflector away from the backlight surface is typically chosen so that the reflector edge 130 is slightly higher than the highest part to be passed under the reflector, including any mountings, frames or other mechanisms required to hold and transport the part thereunto. As such the reflector need not be moved axially (upwardly and downwardly with respect to the base) each time a part passes thereinto. However axial movement of the base and/or reflector is expressly contemplated according to an alternate embodiment where variable clearance is desired. Because the reflector bounces incident light fully to its lower edges, the angle of reflected rays 150 striking the part is significantly lower (with respect to the base/backlight surface) than the prior art (see for comparison, rays 30 in FIG. 1). As such, various side edges 44 and other upright formations on the part 14 are more fully illuminated.

In general, light reflected from the part 14 via the reflector surface has a significantly lower intensity than light transmitted directly from the backlight unit 114 toward the camera lens. This directly transmitted light, if unfiltered, would essentially "blind" the camera, and degrade a proper view of the part. In order to filter any directly transmitted light so that only reflected illumination light is viewable by the camera, a layer of polarizing material 160 is positioned over the surface of the backlight unit so that it is interposed between the backlight units' transmitted light and the camera/reflector assembly. Any commercially available polarizing material can be used. In general, a material with a "plane polarizer" characteristic is employed. For ease of replacement, durability and handling, a polymeric plane-polarizing material is applied to the backlight. However, a glass layer can be used in an alternate embodiment. Accordingly, all light transmitted from the backlight becomes plane-polarized before it strikes the reflector, the part and finally, the camera. A complementary plane polarizer 166 is provided over the camera lens 35 in a preferred embodiment this plane polarizer is constructed from glass to camera optical quality specifications. The polarizer 166 in the camera is aligned so that directly transmitted light from the backlight unit is filtered-out due to well-known cross-polarizing effects. Conversely, due to the inherent nature of polarized light, the reflected, non-directly transmitted light form the part 14, passes through the polarizer 166 and is received by the camera unit with minimal loss. It is contemplated that some direct light may pass through the filter arrangement, and the filter may attenuate some reflected light. In general, however, a substantial amount of direct light is blocked, while a fairly substantial portion of reflected light passes. The resulting image accurately captures details of the part, including those details requiring lower-angle illumination.

The intensity of light transmitted from by the backlight unit is variable by, for example changing the output or bulb wattage of the light source. In addition, a variety of color filters can be interposed between the light source and the backlight to further optimize illumination for a particular part. As such, the above-described system provided enhanced versatility over conventional prior art systems as well as wider angle of illumination.

The foregoing has been a detailed description of the preferred embodiment of the invention. The various modifications and additions can be made without departing from the spirit and scope of the invention. For example, while a single, square-shaped backlight unit is detailed, a multi-part backlight, or a backlight having a customized shape can be employed according to an alternate embodiment. Additionally, an inspection system according to this invention can be built integrally into a part transport mechanism or, alternatively, the entire inspection system can be made moveable to pass into and out of a production line as needed, effectively passing under each part to perform inspection, rather than requiring each part to be passed thereunder. Furthermore, while a polarizer is located on the lens of a camera according to the illustrated embodiment, a polarizer can be mounted over the aperture separately and any viewing device, including a bare human eye, can be positioned to view the part through the aperture. The reflector aperture can also comprise an opening in the reflector or a transparent material that defines a sealed window. Also a plurality of camera assemblies and/or a plurality of apertures can be defined on the reflector to provide multiple angle viewing of the part. Finally, while a plane polarizer is illustrated, any filter that selectively cancels or reduces direct light while allowing a significant amount of reflected light to pass therethrough can be substituted.

Accordingly, this description is meant to be taken only by way of example and not to otherwise limit the scope of the invention.

What is claimed is:

1. An apparatus for providing diffuse illumination to a part comprising:

a reflector located over the part having an aperture for viewing the part there-through, the reflector defining a lower perimeter edge;

an inner surface of the reflector for reflecting diffuse light onto predetermined portions of the part;

a backlight located opposite the inner surface and facing the lower perimeter edge, the blacklight arranged so that the part is positioned between the backlight and the inner surface, the part overlying a portion of the backlight, the backlight comprising a continuous light panel having a diffuser face that generates a diffuse uniform light, the diffuser face extending at least to the lower perimeter edge;

a first filter located on the diffuser face, the first filter extending at least to the lower perimeter edge, for providing transmitted light from the backlight with a predetermined characteristic; and a second filter located at the aperture constructed and arranged for canceling light directly received from the backlight with the predetermined characteristic and enabling a substantial portion of light reflected from the reflector, and transmitted onto the part, to be received through the second filter.

2. The apparatus as set forth in claim 1 wherein each of the first filter and the second filter comprises a polarizer, each being oriented in a predetermined relationship so as to filter direct light transmitted therebetween.

3. The apparatus as set forth in claim 2 further comprising a camera assembly positioned to receive light from the second filter.

4. The apparatus as set forth in claim 3 wherein the backlight includes a grid of light sources located beneath the diffuser face on a side of the diffuser face opposite a side adjacent to the first filter.

5. The apparatus as set forth in claim 4 wherein each of the light sources comprises a fiber optic having a tip for transmitting light there-from toward the diffuser face, and further comprising a cable for enclosing each fiber optic and a light source for providing light to the cable.

6. The apparatus as set forth in claim 1 wherein the reflector comprises a hemisphere located to overlie the backlight.

7. The apparatus as set forth in claim 6 wherein the aperture is located adjacent an apex of the hemisphere.

8. The apparatus as set forth is claim 6 wherein the lower perimeter edge is located at a spacing with respect to each of the backlight and the first filter arranged to allow a predetermined part to pass thereunder.

9. The apparatus as set forth in claim 6 wherein the inner surface of the reflector comprises a matte white light-diffusing coating thereon.

10. A method for illuminating a part for inspection thereof comprising:

provinding a backlight that defines a continuous light panel with a diffuser face that generates a diffuse uniform light over the diffuser face;

positioning a hemispherical reflector surface over the diffuser face with a lower perimeter edge at a spacing from the diffuser face, the diffuser face extending outwardly at least to the perimeter edge;

positioning a part over the backlight so that the part overlies a portion of the diffuser face;

transmitting the diffuse uniform light from an upper surface of the backlight toward the reflector surface that overlies the backlight and the part;

providing a first filter, located on the backlight and extending at least to the perimeter edge, to generate transmitted light from the backlight with a predetermined characteristic; and viewing the part through a second filter located at an aperture on the reflector surface, wherein a substantial portion of light directly received from the backlight is blocked by the second filter and a substantial portion of light reflected from the reflector surface, and transmitted onto the part, is passed through the second filter.

11. The method as set forth in claim 10 further comprising positioning a camera at the aperture.

12. The method as set forth in claim 11 further comprising defining an apex in the reflector surface more remote from the backlight than the lower perimeter edge, and locating the aperture at the apex.

13. The method as set forth in claim 12 further comprising selectively passing the part under the lower perimeter edge at predetermined times for inspection of the part.

14. The method as set forth in claim 12 further comprising supporting the part with respect to the upper surface of the backlight.

15. The method as set forth in claim 10 further comprising selecting the first filter and the second filter each as a polarizer and orienting the first filter with respect to the second filter so that light transmitted directly from the first filter to the second filter is substantially blocked.

16. The apparatus as set forth in claim 1 wherein the backlight is adapted to support the part directly thereon.

17. The apparatus as set forth in claim 1 wherein the diffuser face and the first filter extend outwardly beyond the lower perimeter edge.

18. The method as set forth in claim 10 further comprising supporting the part directly upon the backlight.

19. The method as set forth in claim 10 wherein the step of providing the backlight includes arranging a plurality of light sources adjacent the diffuser surface so as to define the uniform diffuse light thereon.

* * * * *